(12) United States Patent
Gao

(10) Patent No.: US 9,395,370 B2
(45) Date of Patent: Jul. 19, 2016

(54) PURIFICATION OF MONOCLONAL ANTIBODIES

(75) Inventor: Qian Gao, San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 781 days.

(21) Appl. No.: 12/831,458

(22) Filed: Jul. 7, 2010

(65) Prior Publication Data

US 2011/0009287 A1 Jan. 13, 2011

Related U.S. Application Data

(60) Provisional application No. 61/223,984, filed on Jul. 8, 2009.

(51) Int. Cl.
*G01N 33/577* (2006.01)
*C07K 16/06* (2006.01)
*C40B 30/04* (2006.01)

(52) U.S. Cl.
CPC ............ *G01N 33/577* (2013.01); *C07K 16/065* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 5,891,647 | A | 4/1999 | Lormeau et al. |
| 6,770,445 | B1 | 8/2004 | Scholer et al. |
| 2003/0044849 | A1* | 3/2003 | Kessler ............... C07K 16/005 435/7.1 |
| 2003/0059764 | A1 | 3/2003 | Ravkin et al. |
| 2003/0143612 | A1* | 7/2003 | Ault-Riche et al. .............. 435/6 |
| 2007/0237713 | A1 | 10/2007 | Fan et al. |
| 2008/0213277 | A1 | 9/2008 | Sasu et al. |

FOREIGN PATENT DOCUMENTS

| | | |
|---|---|---|
| JP | 2006-193485 A | 7/2006 |
| JP | 2008-506352 A | 3/2008 |
| WO | WO 00/54724 A2 | 9/2000 |
| WO | WO 2005/116076 A2 | 12/2005 |

OTHER PUBLICATIONS

2008 Protein A, G, L immunoreactants from Uptima.*
Kohno et al (1987 Hiroshima Journal of Medical Science 36:36-46).*
Zhang et al (2008 Chinese Journal Biologics 21:999-1001).*
Supplementary European Search Report from EP 10797757, dated Jan. 24, 2013 (6 pages).
Akhoundi et al.; "Production and characterization of monoclonal and polyclonal antibodies to human α2-HS: development of a two-site ELISA test"; *J. Immunol. Meth.*; 172:189-196 (1994).
Cajot et al.; "Monoclonal antibodies directed against human tissue-type plasminogen activator: a characterization of their species, specificity, affinity and heavy-chain binding"; *Thrombosis Research*; 46:141-152 (1987).
Gaillard et al.; "Analysis of inactive renin by renin profragment monoclonal antibodies"; *FEBS*; 207(1):100-104 (1986).
Muronetz et al.; "Isolation of antigens and antibodies by affinity chromatography"; *J. Chromatocr. B*; 790:53-66 (2003).
Thomas et al.; "Monoclonal antibody ARC MAC 50.1 binds to a site on the phytochrome molecule which undergoes a photoreversible conformational change"; *FEBS*; 195(1,2):174-178.
Ohmi, S. et al., "Experimentation Protocols for Anti-Peptide Antibodies," Cell Engineering (in Japanese), Supplementary Volume (new version), pp. 81-83, Shujunsha Co., Ltd., Sep. 6, 2004 (2nd Edition).

* cited by examiner

*Primary Examiner* — Christopher M Gross
(74) *Attorney, Agent, or Firm* — Kilpatrick Townsend and Stockton LLP

(57) ABSTRACT

Methods and compositions for efficiently purifying monoclonal antibodies and identifying pairs of antibodies compatible in sandwich immunoassays are provided.

18 Claims, 1 Drawing Sheet

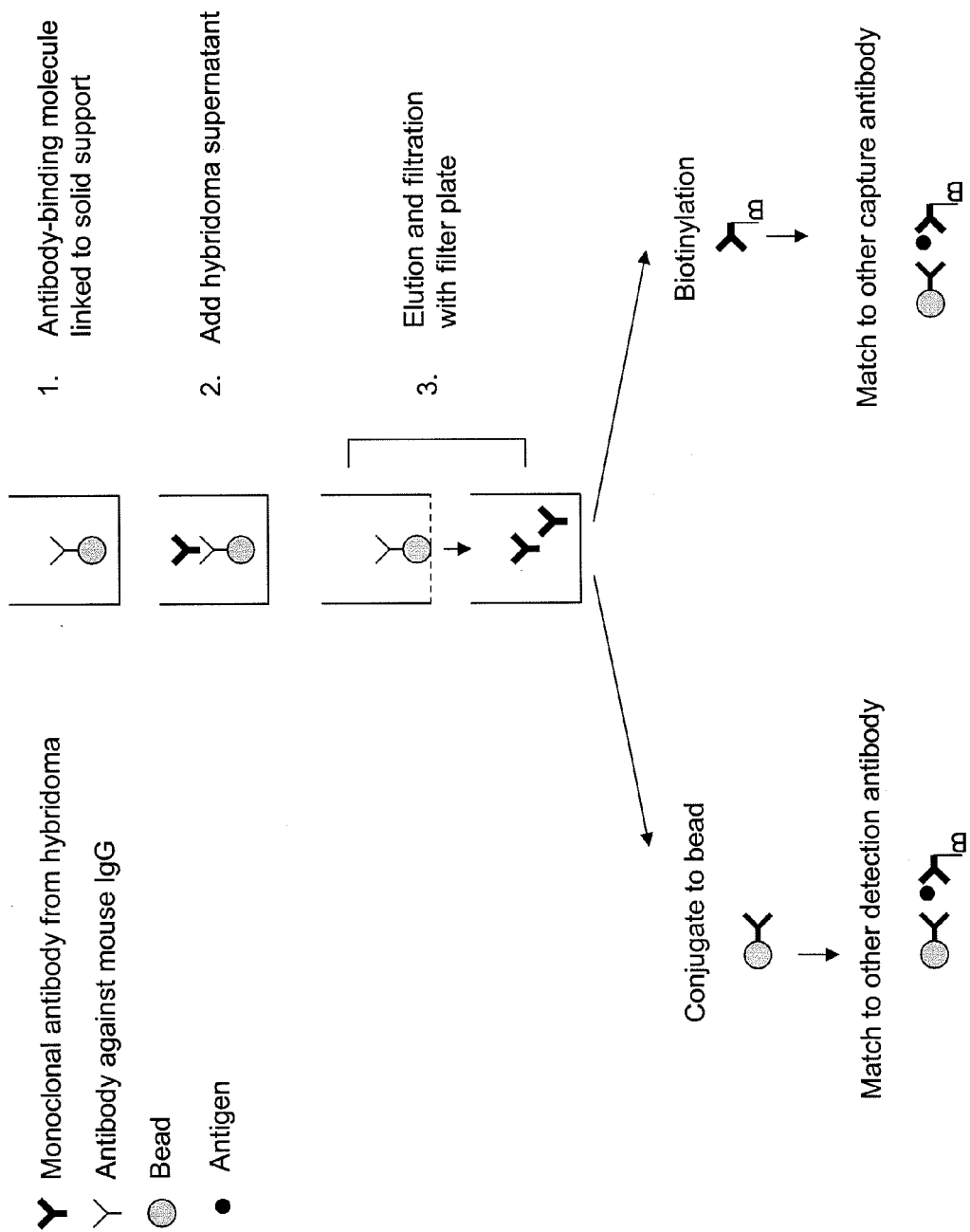

PURIFICATION OF MONOCLONAL ANTIBODIES

CROSS-REFERENCE TO RELATED PATENT APPLICATIONS

The present application claims benefit of priority to U.S. Provisional Patent Application No. 61/223,984, filed Jul. 8, 2009, which is incorporated by reference.

BACKGROUND OF THE INVENTION

Monoclonal antibodies are proteins with high specificity and sensitivity in their reactions with specific sites on target molecules. Monoclonal antibodies are generally produced by somatic cell clones of splenocytes fused to multiple myeloma-derived cells (hybridomas) (Kohler and Milstein, *Nature* 256 (5517): 495 (1975)).

BRIEF SUMMARY OF THE INVENTION

The present invention provides for methods of identifying a pair of monoclonal antibodies for use in a sandwich immunoassay prior to the establishment of hybridoma clones. In some embodiments, the method comprises in the following order,
(a) contacting an array of different hybridoma culture supernatants to an array of antibody-binding molecules, wherein the antibody-binding molecules are linked to a solid support, under conditions to allow for binding of an antibody in the supernatant to the antibody-binding molecule;
(b) separating unbound components of the supernatants from the support;
(c) altering the conditions of solution surrounding the solid support, thereby eluting the antibody from the antibody-binding molecules,
(d) separating the solid support from the solution comprising the eluted antibodies to create an array of elutions comprising antibodies from the hybridomas; and
(e) determining the ability of a first antibody in the array of elutions to bind to an antigen in the presence of a second antibody that binds the antigen, thereby identifying a pair of monoclonal antibodies for use in a sandwich immunoassay.

In some embodiments, step (d) comprises filtering the solution comprising the eluted antibodies and the solid support such that the antibody flows through a filter, wherein the support is blocked by the filter. Thus, the array of elutions are an array of "filtrates."

In some embodiments, step (d) comprises magnetic separation of the solid support from the solution comprising the eluted antibodies.

In some embodiments, the hybridoma clones are generated from non-clonal hybridoma cultures.

In some embodiments, the solid support is a bead. In some embodiments, the bead is an agarose bead, a polystyrene bead, a magnetic bead, or a paramagnetic bead.

In some embodiments, the antibody-binding molecule is selected from the group consisting of an antibody, protein A, protein G, and an antigen.

In some embodiments, steps (a)-(d) are performed in a multi-well format such that different wells comprise different antibodies from different hybridomas.

In some embodiments, the filtering comprises vacuum-assisted filtering.

In some embodiments, after step (d), the antibodies are linked to a solid support or biotinylated.

In some embodiments, step (e) comprises performing a sandwich immunoassay in which antibodies from the array are used as different capture antibodies in the immunoassay and a second antibody is used as a primary detection antibody. In some embodiments, the capture reagents are linked to a solid support. In some embodiments, the primary detection antibodies are biotinylated.

In some embodiments, step (e) comprises performing a sandwich immunoassay in which antibodies from the array is used as different primary detection antibodies in the immunoassay and a second antibody is used as a capture antibody. In some embodiments, the capture reagents are linked to a solid support. In some embodiments, the primary detection antibodies are biotinylated.

In some embodiments, step (e) comprises performing a sandwich immunoassay in which a first aliquot of antibodies from the array is used as a capture antibody in the immunoassay and a second antibody aliquot of antibodies from the array is used as primary detection antibodies. In some embodiments, the capture reagents are linked to a solid support. In some embodiments, the primary detection antibodies are biotinylated.

In some embodiments, the method further comprises establishing hybridoma clones from hybridomas determined to produce a first antibody or second antibody that binds to the antigen.

It will be appreciated from a review of the remainder of this application that further methods and compositions are also part of the invention.

DEFINITIONS

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, particularly those that retain antigen-binding function.

The phrase "specific binding" refers to a binding reaction where two members of a binding pair (e.g., an antibody and a molecule comprising the antibody's target epitope) bind to each other with an affinity that is at least 100-fold better than the members' affinity for other components of a heterogeneous mixture (e.g., a hybridoma culture supernatant or other mixture of proteins).

A "solid support" refers to a material or group of materials having a rigid or semi-rigid surface or surfaces. In some embodiments, the solid support takes the form of thin films or membranes, beads, bottles, dishes, fibers, woven fibers, shaped polymers, particles, and microparticles, including but not limited to, microspheres. A solid support can be formed, for example, from an inert solid support of natural material, such as glass and collagen, or synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. Frequently, some functional groups, e.g., carboxylic acid (—COOH), free amine (—NH2), and sulfhydryl (—SH) groups, naturally present on the surface of a carrier can be used for peptide linkage. In case no such functional group is naturally available, a desired functional group, such as a carboxylic acid group, or a moiety known to be a partner of a binding interaction (such as avidin that is capable of binding biotin) may be attached to such solid support. In some embodiments, the solid support is a carboxylated latex or magnetic microsphere.

BRIEF DESCRIPTION OF THE DRAWINGS

FIG. 1 provides a representational drawing of an embodiment of the invention.

DETAILED DESCRIPTION

I. Introduction

The present invention provides for an efficient method for purification of antibodies from hybridomas or other antibody solutions (including but not limited to polyclonal antibody solutions) and subsequently identifying pairs of antibodies that bind the same antigen and are useful, for example, for sandwich immunoassays. There are a number of different formats for sandwich immunoassays, but a common theme is the binding of two different antibodies ("antibody pairs") to the same antigen. Antibody pairs generally bind to different epitopes and therefore do not significantly compete with each other for binding to the antigen. The present invention provides for an efficient method of selecting monoclonal antibodies that function well as antibody pairs in a sandwich immunoassay without requiring large volumes or quantities of antibody or many purification steps.

The present invention provides for methods that involve reversible binding of antibodies in antibody solutions (including but not limited to, hybridoma culture supernatants) to a solid support, separating the bound antibody and solid support from other components of the supernatant, and subsequently separating the antibody from the solid support under elution conditions to produce an array of solutions comprising different purified antibodies. The latter separating step can include, but is not limited to filtration of the solid support (e.g., beads) or magnetic separation. Notably, the antibody purification methods of the invention can be applied very early in hybridoma development (e.g., prior to establishment of hybridoma clones), thereby allowing for screening of antibodies and identification of hybridomas of interest before the need for hybridoma cloning steps. This method therefore greatly reduces the labor typically involved in cloning numerous hybridomas prior to screening.

The solutions of purified antibodies can be divided into portions such that the antibodies in one portion are modified with a first modification and antibodies in a second portion are modified with a second modification. A sandwich immunoassay can then be employed to make pair-wise comparisons between different antibodies, wherein one of the pairs of antibodies has a first modification and the other antibody of the pair has the second modification. Optionally, 10s, 100s, 1000s, or more pairwise comparisons can be made according to the method of the invention. This method thereby allows for pairwise comparisons of different antibodies in an array to identify pairs of antibodies, and corresponding hybridomas providing the antibodies, that are useful in a sandwich immunoassay.

II. Purification of Antibodies

The present method allows for purification of antibodies in a fast and efficient process to generate purified antibodies that can be used directly for conjugation and optionally, subsequent pairwise comparisons. In some embodiments, the antibodies are purified from polyclonal antibodies or other antibody sources. Notably, the invention is of particular use in purifying a large number of different antibodies in parallel from a small volume source. Thus, in some embodiments, the invention is of particular use for purifying and screening binding properties of antibodies from hybridomas.

A variety of methods are known and can be used for generating hybridomas or other antibody-producing cells. See, e.g., Harlow, ANTIBODIES, Cold Spring Harbor Press, N.Y. (1989). In some embodiments, to generate hybridomas producing monoclonal antibodies to an antigen, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag14 myeloma cells (ATCC, CRL 1581) with 50% PEG (w/v). Cells can be plated at approximately $1 \times 10^5$ per well in flat bottom microtiter plate, followed by a two-week incubation in selective medium containing besides usual reagents 10% fetal Clone Serum, 5 Origen Hybridoma Cloning Factor (IGEN) and 1×HAT (Sigma). After approximately two weeks, cells can be cultured in medium in which the HAT is replaced with HT (Sigma).

Optionally, hybridomas used in the methods of the present invention have been pre-selected for production of antibodies against a desired target. Thus, in some embodiments, all or a majority of the hybridomas in the method are known to bind to a particular antigen. Alternatively, the affinity or target of antibodies produced by the hybridomas is not known. In the latter case, generally a significantly larger number of additional hybridomas will be screened than if the hybridomas are known to produce antibodies that bind the antigen of interest. If desired, screening methods for initially identifying hybridomas that produce antibodies that bind an antigen can be used. As discussed above, an advantage of the present method is that one does not need to generate hybridoma clones (i.e., clonal cell populations) until after screening the antibodies for reactivity. This eliminates the step of generating and screening a large number of clonal hybridoma lines because screening can occur before the clonal lines are developed. Once a particular hybridoma supernatant is determined to contain antibodies of interest (e.g., by using the screening methods described herein), hybridoma clones can then be generated from those hybridomas that generated the positive supernatant.

Ideally, a plurality of hybridoma culture supernatants (or other antibody solutions) can be screened in parallel according to the method of the invention. Thus, in some embodiments, hybridomas are cultured in multi-well containers or are otherwise grown in parallel to allow for ease of manipulating a number of mixtures in parallel. Initially, an aliquot of hybridoma supernatant (or other antibody solutions) containing antibodies is contacted to a first reagent linked to a solid support, wherein the first reagent has an affinity for (i.e., specifically binds) the antibodies. The solid support can include, but is not limited to, a bead or microparticle, or other solid support that can be suspended in a solution but does not pass through a filter as described below. Such reagents can include, for example, another antibody specific for the species from which the hybridomas were derived (e.g., an anti-mouse antibody generated in a non-mouse animal). Alternatively, in some embodiments, the first reagent with affinity for the antibodies is selected from the group consisting of: protein A, protein G, and an antigen or other epitope-containing molecule. In the latter case, the antigen can be the antigen to which the sandwich immunoassay will ultimately be directed.

The first reagent linked to a solid support is contacted to the hybridoma supernatant (or other antibody solution) for a sufficient time and under conditions to allow for binding of antibodies in the supernatant to the first reagent. Other non-antibody components of the supernatant can then be separated from the antibodies bound to the first reagent by taking advantage of methods that can separate the solid support from components of the solution not bound to the first reagent. Optionally, vacuum filtration is used to separate the solid support (and first reagent and antibodies bound thereto) from non-antibody components of the supernatant. Filter plates, for example as are known in the art, can be useful for such separations.

A number of methods of separating solution components are known. Physical separation methods can include, for example, centrifugation to pellet the solid supports (e.g., beads) followed by removal of the supernatant and optionally one or more wash steps under conditions to maintain binding of the antibodies to the first reagent can be employed. In some embodiments, the solid support will comprise a magnet or magnetic material. In these optional embodiments, magnetic forces can be used to fix the solid support to a container allowing for convenient removal of the supernatant and optional wash fluids without removal of the solid support. Magnetic solid supports are described in, for example, US Patent Publication 2005/0266462, though those of skill in the art will appreciate that other magnetic formulations are also possible.

The antibodies/first reagent/solid support can be optionally washed one or more times, in a solution that does not substantially elute the antibodies from the first reagent, to remove residual hybridoma supernatant if desired.

Following the optional wash steps, the antibodies bound to the first reagent, which is linked to the solid support, are submitted to conditions to allow for elution of the antibodies from the first reagent. Such conditions can vary depending upon the first reagent and its interaction with the target antibodies. In some embodiments, the elution conditions comprise a raised temperature (relative to previous wash conditions) and/or change in (e.g., lowering the) pH, thereby reducing the binding between the antibodies and first reagent. If the pH is lowered to elute the antibodies, optionally a neutralization solution can be subsequently added to protect the antibodies from long term acid exposure.

Following elution of the antibodies from the first reagent, the solution containing the antibodies and first reagent is separated from the solid support. In some embodiments, the solution comprising the eluted antibodies and solid support is filtered, i.e., the solution can be filtered to remove the first reagent linked to the solid support. By selecting a filter that blocks passage of the solid support and allows for passage of the eluted antibodies, the antibodies can be separate from the first reagent, thereby purifying the antibodies from the hybridomas. A variety of filtering apparatuses can be used as is known in the art. In some embodiments, a multi-well filter plate is used to filter multiple different antibodies separately in parallel. A variety of filter plates are known and are commercially available, e.g., from Pall Corp., Millipore, Quality Scientific Plastics, etc.

Optionally, other methods can be used to separate the solution comprising the eluted antibodies from the solid support. For example, magnetic separation methods can be employed.

In some embodiments, the filterplate is used for capturing the solid support while allowing the eluted antibody to pass through to a collection reservoir or tube. For example, in some embodiments, a filterplate is a multi-well (e.g., 96-well) plate with a glass fiber or other type of filter membrane attached at the bottom. A mixture comprising the first reagent (and solid support) and antibodies (either linked or eluted) is applied to the filterplate, optionally under conditions to allow for elution of the antibodies from the first reagent if not eluted already, such that the solid support is trapped on or in the membrane. Optionally, vacuum filtration can be applied to pull solution comprising the eluted antibodies through the filter. The eluted antibodies, substantially free of the first reagent and solid support, are then collected. Optionally, the different antibodies from the different hybridomas are collected in a multi-well microtiter dish or other collection reservoir that allows for organization of the separate antibodies so that one identify and use the producing hybridoma once a specific antibody is found to have a desired reactivity.

III. Methods for Determining Antibody Binding

Following collection of the purified antibodies from hybridomas as described above, pairs of collected antibodies can be compared for their compatibility for use together in a sandwich immunoassay. Optionally, one can take aliquots of the antibodies purified as described above, without further intervening steps, and prepare them for use in an immunoassay, e.g., link the antibodies to a solid support or a detectable label such as biotin.

A sandwich immunoassay refers to an assay for a target molecule, wherein a capture antibody is linked to a solid surface, a mixture possibly containing the target is contacted to the first antibody, washed, and then contacted with one or more further detection reagents to detect the presence or amount of the target bound to the capture antibody. In the methods of the present invention, the primary detection reagent, i.e., the reagent that binds the captured target molecule, is also an antibody, e.g., purified from hybridomas, optionally as described above. Thus, the present invention allows for selection of compatible antibody pairs for a sandwich immunoassay for a target molecule, wherein one member of the pair is the capture antibody and the second member of the pair is the primary detection antibody.

The present invention can take advantage of the above-described antibody purification methods and use the thus-purified antibodies to determine compatible antibody pairs in an immunoassay. In some embodiments, one capture antibody is used and paired in an immunoassay with a plurality of different antibodies, functioning as primary detection antibodies, that are purified from the hybridomas as described above. Alternatively, in some embodiments, a plurality of different capture antibodies, purified from different hybridomas as described above, are paired with one primary detection antibody in a sandwich immunoassay. Optionally, a plurality of antibodies purified as described above can be used as capture and primary detection antibodies to identify an optimal binding pair.

In some embodiments, the capture antibody is linked to a solid support. In some embodiments of the invention, an aliquot of purified antibody from the hybridomas is taken and linked to a solid support to form an array of different antibodies bound to a solid support. A variety of different solid supports can be used, including but not limited to beads, optionally magnetic beads, or other solid supports as described above. In some embodiments, the solid support comprises polysteryne. Optionally, different antibodies are linked to different solid supports, for example solid supports that can be distinguished by flow cytometry, e.g., due to size of the label linked to such support. See, e.g., U.S. Pat. Nos. 7,271,009; 6,872,578; and WO 02/075311.

Numerous methods are known in the art for linking antibodies to a solid surface. As one example, a linking agent (including but not limited to N-hydroxisulfosuccinimide (NHSS) optionally with 1-Ethyl-3-[3-dimethylaminopropyl] carbodiimide hydrochloride (EDC)) can be used to link an antibody to a solid support.

In some embodiments, a second aliquot of purified antibody from the hybridomas is taken and used as the primary detection antibody in an immunoassay. In some embodiments, antibodies from the aliquot are linked to a directly- or indirectly-detectable label to form the primary detection antibody. A directly detectable label is a reagent that generates a signal directly. For example, a fluorescent tag is directly detectable. Optionally, the antibody is linked to an indirectly detectable label, e.g., an affinity agent. Affinity agents include, but are not limited to, biotin, avidin or strepavidin.

The compatibility of two different antibodies to function in a sandwich immunoassay can be determined, for example, by using one, or an array of, capture antibodies (e.g., as described above), in a sandwich immunoassay combined with one, or an array of, primary detection antibodies optionally derived from the hybridomas. The assay can include, for example, contacting a known amount of target antigen to the capture antibodies (linked to the solid support) under conditions to allow for the target to bind the capture antibody, optionally washing the excess target from the solid support, and then contacting the primary detection antibody to the bound target. The presence, absence, or amount of the primary detection antibody will indicate the compatibly of the capture and primary detection antibodies. Problems can occur, for example, where the two antibodies compete for binding to the same epitope or where binding by the capture antibody does not allow for availability of the primary detection antibody target epitope. Thus, by comparing one or a plurality of candidate capture antibodies in the sandwich immunoassay to one or a plurality of candidate primary detection antibodies, one can quickly and efficiently identify which antibody pairs are compatible and optionally, which pair is "best", i.e., provides for optimal detection or accurate determination of quantity of the target.

A number of sandwich immunoassays are known and can be used to determine compatibility of two antibodies. In an exemplary microtiter plate sandwich immunoassay, a monoclonal capture antibody is adsorbed onto a plastic microtiter plate. When the test sample is added to the plate, the antibody on the plate will bind the target antigen from the sample, and retain it in the plate. When a polyclonal antibody is added in the next step, it also binds to the target antigen (already bound to the monoclonal antibody on the plate), thereby forming an antigen 'sandwich' between the two different antibodies. This binding reaction can then be measured by any method known in the art.

For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra).

In some embodiments, the solid support of the immuno assay is one or more bead which is optionally detected by flow cytometry. Where multiple capture antibodies are used, in some embodiments, different beads or other microparticles, distinguishable by flow cytometry, are linked to different capture antibodies. Such technology, is described in, e.g., U.S. Pat. Nos. 7,271,009; 6,872,578; and WO 02/075311 and is available commercially from Bio-Rad (Hercules, Calif.) as the Bio-Plex™ system. Aspects distinguishable by flow cytometry include but are not limited to size and mass of a particle or the wave length of fluorescence of a label on the particle.

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide or a labeled (e.g., biotinylated) antibody that binds the protein of interest. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as avidin or streptavidin. A variety of detectable moieties are well known to those skilled in the art.

Immunoassays include noncompetitive assays and competitive assays. In competitive assays, the amount of polypeptide present in the sample is measured indirectly by measuring the amount of a known, added (exogenous) polypeptide of interest displaced (competed away) from an antibody that binds by the unknown polypeptide present in a sample.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes (e.g., fluorescein isothiocyanate, Texas red, rhodamine, and the like), radiolabels, enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component (e.g., the primary detection antibody) of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize the polypeptide of interest, or secondary antibodies that recognize an antibody that binds the polypeptide.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Methods of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

EXAMPLES

The following examples are offered to illustrate, but not to limit the claimed invention.

A. Reagents & Materials
1. Anti-mouse IgG agarose: Sigma A6531
2. Wash buffer: 0.1M PB (pH7.4), 0.5M NaCl
3. Elution buffer: 0.5M Acetic Acid (pH 2.4)
4. Neutralization buffer: 0.2M PB, 0.5N NaOH (pH 13)
5. Monobasic sodium phosphate solution (100 mM $NaH_2PO_4$, pH 6.0)
6. 0.1M MES buffer (pH6.0)
7. Tris 1 Storage Buffer (200 mM Trisma Base, 0.1% BSA, 0.3M NaCl, 0.1% Proclin, 0.02% Tween 20, 0.1% $NaN_3$, pH 7.4)
8. Dynal MPC-S magnetic bead separator (Bynal Biotech, cat# 120-20D)
9. 2 ml screw cap microcentrifuge tubes with O-ring caps, sterile (VWR, cat# 89004-298) for beads coupling
10. Microtiter Shaker (IKA Works, Model MTS 2/4 digital, cat# 3208001)
11. Collection Tubes with Rack (QSP Quality Scientific Plastics, Cat#: 84501XNBZQ, rack with 1.2 mL micro titertubes; VWR 82006-700)
12. Luminex Magnetic Beads (Luminex MagPlex™ Microsphere, cat. Number: 1 ml MC10xxx-01 (where xxx is the bead region number)
13. N-hydroxysulfosuccinimide (NHSS, Pierce, cat#: 24510)
14. 1-ethyl-3-(3-dimethylaminopropyl) carbodiimide hydrochloride (EDC, Pierce, cat#: 22980)
15. Sulfo-NHS-Biotin (Pierce, cat#: 21217)
16. Bio-Plex Pro™ Cytokine Reagent Kit 10×96 well (Bio-Rad, cat#: 171-304071)

B. Antibody Purification

The volume of anti-mouse IgG agarose needed is calculated as follows: Volume of anti-mouse IgG agarose (μL)=numbers of samples×10.

The volume of wash buffer is calculated as: Volume of wash buffer (μL)=numbers of samples×40.

The calculated amount of wash buffer and anti-mouse IgG agarose are mixed in a clean tube. Filter plate wells are pre-wet with 100 μL of wash buffer and subsequently vacuum is applied to remove the buffer. The anti-mouse IgG agarose is vortexed well and 50 μL is added into each well of the filter plate. Vacuum is applied to remove the buffer.

250 μL of wash buffer is added to each well and vacuum is applied to remove the buffer. The 250 μL of hybridoma supernatant is added into the wells. The resulting mixture is shaken at speed 900 for 45 minutes.

Vacuum is applied to remove the supernatants. Another 250 μL of supernatant is added, again shaken for 45 minutes and the vacuum is applied again to remove the supernatants.

Subsequently, 250 μL of wash buffer is added to each well and vacuum is applied to remove the buffer. This step is repeated two more times.

60 μL of Neutralization Buffer is added to each collecting tube. 60 μL of Elution Buffer is added into each well and the plate is shaken with speed set at 1100 for 1 minute.

A 96 well QSP (Quality Scientific Plastics, Cat#: 84501XNBZQ) rack with 1.2 mL micro titertubes is put onto a in a Bio-Rad vacuum manifold (Cat#: 732-6470). The filter plate is put on top of QSP tubes, ensuring the well bottoms are matched to tubes accordingly.

Vacuum is applied to collect the antibody into collection tubes and immediately shaken at speed of 900 for one minute to neutralize the pH. Twenty microliters of water is added into each tube and mixed well.

Twenty microliters of purified antibody from each purification can subsequently be applied for bead conjugation and the remainder (about 120 μL) can be used for biotinylation.

C. Purified Antibody Conjugated to Polysteryne Beads

Bead volume needed is calculated as follows: bead volume needed (μL)=sample number×2.2 (This calculation is based on 22 tests derived from one sample, theoretically it will be 1250 beads/well for the Bio-Plex run).

The beads are vortexed well and the magnetic beads are pipetted into a 2 mL tube. 150 μL of diH2O is added into the tube and mixed well. The magnet separator is applied for 30 seconds and the solution is subsequently removed, ideally without touching the beads. The tube is removed from the magnet separator and 80 μL of 100 mM Monobasic Sodium Phosphate solution is added to resuspend beads.

Fresh NHSS and EDC solutions are prepared. One milligram of NHSS is dissolved into 20 μL 100 mM monobasic sodium phosphate solution. One milligram of EDC is dissolved into 20 μL 100 mM monobasic sodium phosphate solution.

Ten microliters of NHSS is added into the bead solution and mixed well. Ten microliters of EDC is subsequently added to the bead solution and mixed well. The beads are then shaken in dark at 900 for 20 minutes.

A magnet separator is applied for 30 seconds and the solution is removed from the tube. The beads are then resuspended in 150 uL 0.1M MES buffer (pH 6.0). The magnet separator is once again applied for 30 seconds and the solution is removed from the tube. The MES buffer wash and solution removal is then repeated to more fully wash the beads.

The beads are then Resuspended into 0.1M MES buffer (pH 6.0) as follows: Volume of 0.1M MES (uL) needed=number of sample×15.

The beads are mixed well and 15 uL of the bead suspension is added into each tube with 20 uL of purified antibody (purified as discussed above). The tubes are covered with parafilm and shaken in the dark at 900 for 1.5 hours. One hundred eighty-five microliters of Tris storage buffer/tube is added and the beads are stored in the dark at 4° C. The beads can subsequently be used in sandwich or other immunoassays, for example as capture reagents.

D. Biotinylation of Purified Antibody

Ten millimolar Sulfo-NHS-Biotin is prepared. One milligram of Sulfo-NHS-Biotin is dissolved into 227 μL diH2O. 2.4 μL Sulfo-NHS-Biotin (10 mM) is added into 140 μL of purified antibody. The final concentration of biotin is 0.2 mM. The tubes are covered with parafilm and shaken them at 900 for 1.5 hour. One hundred microliters of 1% BSA in PBS is added with 0.02% $NaN_3$ into each tube and the tubes are stored at 4° C.

The biotinylated antibodies can subsequently be used in sandwich or other immunoassays, for example as primary detection antibodies and/or capture antibodies. In some embodiments, the sandwich immunoassay is performed substantially as described in U.S. Pat. No. 7,271,009.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying a pair of monoclonal antibodies for use in a sandwich immunoassay prior to the establishment of individual hybridoma clones, the method comprising in the following order,
    (a) contacting an array of non-clonal different hybridoma culture supernatants to an array of antibody-binding molecules, wherein the antibody-binding molecules are linked to a solid support, under conditions to allow for binding of antibodies in the supernatant to the antibody-binding molecule, wherein hybridomas in the hybridoma cultures were not previously isolated to form clonal lines;
    (b) separating unbound components of the supernatants from the support;
    (c) altering the conditions of solution surrounding the solid support, thereby eluting polyclonal antibodies from the antibody-binding molecules,
    (d) separating the solid support from the solution comprising the eluted polyclonal antibodies of step (c) to create an array of elutions comprising antibodies from the hybridomas; and
    (e) determining the ability of a first antibody in the array of elutions to bind to an antigen in the presence of a second antibody that binds the antigen, thereby identifying a pair of monoclonal antibodies for use in a sandwich immunoassay.

2. The method of claim 1, wherein step (d) comprises filtering the solution comprising the eluted polyclonal antibodies and the solid support such that the polyclonal antibodies flow through a filter, wherein the support is blocked by the filter.

3. The method of claim 1, wherein step (d) comprises magnetic separation of the solid support from the solution comprising the eluted antibodies.

4. The method of claim 1, wherein the solid support is a bead.

5. The method of claim 1, wherein the bead is an agarose bead, a polystyrene bead, a magnetic bead, or a paramagnetic bead.

6. The method of claim 1 wherein the antibody-binding molecule is selected from the group consisting of an antibody, protein A, protein G, and an antigen.

7. The method of claim 1, wherein steps (a)-(d) are performed in a multi-well format such that different wells comprise different antibodies from different hybridomas.

8. The method of claim 2, wherein the filtering comprises vacuum-assisted filtering.

9. The method of claim 1, wherein after step (d), the antibodies are linked to a solid support or biotinylated.

10. The method of claim 1, wherein step (e) comprises performing a sandwich immunoassay in which antibodies from the array of elutions are used as different capture antibodies in the immunoassay and the second antibody is used as a primary detection antibody.

11. The method of claim 1, wherein step (e) comprises performing a sandwich immunoassay in which antibodies from the array of elutions are used as different primary detection antibodies in the immunoassay and the second antibody is used as a capture antibody.

12. The method of claim 1, wherein step (e) comprises performing a sandwich immunoassay in which a first aliquot of antibodies from the array of elutions is used as a source for capture antibodies in the immunoassay and a second aliquot of antibodies from the array of elutions is used as a source for primary detection antibodies.

13. The method of any of claims 10-12, wherein the capture reagents are linked to a solid support.

14. The method of claim 13, wherein the primary detection antibodies are biotinylated.

15. The method of claim 1, further comprising establishing hybridoma clones from hybridomas determined to produce a first antibody or second antibody that binds to the antigen.

16. The method of claim 9, wherein after step (d), the antibodies are linked to a solid support.

17. The method of claim 9, wherein after step (d), the antibodies are biotinylated.

18. The method of claim 1, wherein after step (d), the first antibody is labeled for detection.

* * * * *